US010023858B2

(12) United States Patent
Canady et al.

(10) Patent No.: US 10,023,858 B2
(45) Date of Patent: Jul. 17, 2018

(54) SYSTEM AND METHOD FOR SELECTIVE ABLATION OF CANCER CELLS WITH COLD ATMOSPHERIC PLASMA

(71) Applicant: U.S. Patent Innovations, LLC, Takoma Park, MD (US)

(72) Inventors: Jerome Canady, Lakeland, FL (US); Alexey Shashurin, Rackville, MD (US); Michael Keidar, Baltimore, MD (US); Taisen Zhuang, Rockville, MD (US); Arpitha Parthasarathy, Takoma Park, MD (US)

(73) Assignee: U.S. Patent Innovations, LLC, Takoma Park, MD (US)

( * ) Notice: Subject to any disclaimer, the term of this patent is extended or adjusted under 35 U.S.C. 154(b) by 0 days.

(21) Appl. No.: 14/934,129

(22) Filed: Nov. 5, 2015

(65) Prior Publication Data

US 2016/0138006 A1 May 19, 2016

Related U.S. Application Data

(63) Continuation-in-part of application No. 14/725,167, filed on May 29, 2015.
(Continued)

(51) Int. Cl.
*A61B 18/12* (2006.01)
*C12N 13/00* (2006.01)
(Continued)

(52) U.S. Cl.
CPC .......... *C12N 13/00* (2013.01); *A61B 18/042* (2013.01); *A61B 18/1206* (2013.01);
(Continued)

(58) Field of Classification Search
CPC .............. A61B 18/042; A61B 18/1206; A61B 2018/00172; A61B 2018/00178;
(Continued)

(56) References Cited

U.S. PATENT DOCUMENTS

| 2010/0145253 | A1* | 6/2010 | Gutsol | A61B 18/042 604/20 |
| 2013/0237982 | A1* | 9/2013 | Rencher | A61B 18/1402 606/39 |

OTHER PUBLICATIONS

Maynard, J.E., "Tuned Transformers . . . Design of these electronic units simplified by means of universal performance curves," General Electric Review, Oct. 1943 pp. 559-609.
(Continued)

*Primary Examiner* — Joseph Stoklosa
*Assistant Examiner* — Tigist Demie
(74) *Attorney, Agent, or Firm* — 24IP Law Group; Timothy R DeWitt

(57) ABSTRACT

A method for elevating a TRAIL-R1 expression in cancer cells to induce apoptosis. The method comprises the steps of receiving electrical energy having a specific voltage, frequency and power from an electrosurgical generator, up-converting the voltage and down-converting the frequency with a high voltage transformer having a primary coil and a secondary coil, the secondary coil having a larger number of turns than the primary coil, applying said converted electrical energy to an electrode in an electrosurgical hand piece, flowing an inert gas through said electrosurgical hand piece to produce a cold plasma at a distal end of said electrosurgical hand piece; and applying said cold plasma to cancer cells for 1 to 3 minutes. The inert gas may comprise, for example, helium or argon. In a preferred embodiment the cold plasma is applied to cancer cells for about 2 minutes.

9 Claims, 18 Drawing Sheets

Related U.S. Application Data

(60) Provisional application No. 62/075,638, filed on Nov. 5, 2014, provisional application No. 62/004,360, filed on May 29, 2014.

(51) Int. Cl.
  *A61B 18/04* (2006.01)
  *A61B 18/14* (2006.01)
  *H05H 1/46* (2006.01)
  *A61B 18/00* (2006.01)

(52) U.S. Cl.
  CPC ............... *A61B 18/14* (2013.01); *H05H 1/46* (2013.01); *A61B 2018/00172* (2013.01); *A61B 2018/00178* (2013.01); *A61B 2018/00583* (2013.01); *A61B 2018/1286* (2013.01); *H05H 2001/466* (2013.01); *H05H 2245/122* (2013.01)

(58) Field of Classification Search
  CPC .......... A61B 2018/00583; A61B 18/14; A61B 2018/1286
  See application file for complete search history.

(56) References Cited

OTHER PUBLICATIONS

Huffman, B., "Parasitic Capacitance Effects in Step-up Transformer Design," Linear Technology, Application Note 39, Feb. 1990.
Transformer and Inductor Design Handbook, Chapter 17 (2004).

* cited by examiner

|  | %No. of cells ±SD Positive for TRAIL R-1 | %No. of Apoptotic cells ± SD Positive for Mitosox &TRAIL R-1 |
|---|---|---|
| ZR-75 BraCa cells line Her+/+ |  |  |
| CAP 60Power | 100 | 85.2 ± 5.2 |
| CAP 40Power | 100 | 87.9 ± 4.63 |
| Positive control H2O2 | 0 | 95 ± 7.0 |
| No Treatment | 88.2 ± 20.5 | 4.4 ± 7.7 |
| Helium | 89.7 ± 7.1 | 0 |
| MCF Normal Breast Epithelial Cells |  |  |
| CAP 60Power | 0 | 1.6 ± 0.2 |
| CAP 40Power | 0 | 3.3 ± 0.5 |
| Positive control H2O2 |  | 90 ± 1.2 |
| No Treatment | 0 | 0 |
| Helium | 0 | 4.5 ± 0.4 |

FIG. 11

| | Plasma length 2cm - ARPE Control Cells | | Plasma length 2cm - Y79 Retinoblastoma cells | |
|---|---|---|---|---|
| Time in Sec | % cell Death CAP | % cell Death He | % cell Death CAP | % cell Death He |
| 5 | 0.39±0.675 | 0.1903±0.33 | 45.28±47.83 | 3.433±3.433 |
| 15 | 0.551±0.55 | 0.401±0.361 | 50.17±48.17 | 14.4±8.591 |
| 20 | 0.311±0.539 | 0.102±0.176 | 56.64±42.35 | 12.03±8.571 |
| 30 | 1.127±1.95 | 0.47±0.429 | 86.81±17.72 | 28.47±16.96 |
| 60 | 1.3±1.69* | 0±0 | 87.86±16.38* | 18.02±13.40 |
| 120 | 2.203±1.97* | 0.843±0.747 | 90.74±16.04* | 33.55±17.99 |
| 180 | 13.28±20.15 | 0.847±0.768 | 100±0 | 47.60±26.12 |
| | | | | |
| H2O2 | 94.18±2.07 | | 94.075±5.55 | |
| No Treatment | 0.543±0.941 | | 22.78±27.35 | |

FIG. 12

| | Helium 2min | 1.6W CAP 2min | H₂O₂ | TNF-α | No Treatment |
|---|---|---|---|---|---|
| Y79 Tumor Cells | A | B | C | D | E |
| ARPE-19 Normal Cells | F | G | H | I | J |
| % TUNEL Positive Y79 Tumor Cells | 5.7 ± 5.05 | 50.3 ± 25.9* | 49.5 ± 26.1 | 27.08 ± 22.3 | 7.73 ± 10.1 |
| % TUNEL Positive ARPE-19 Normal Cells | 0.21 ± 0.36 | 0.98 ± 1.7 | 0 | 0 | 0.06 ± 0.13 |

FIG. 13

| Experiment | Tortuous Displacement (um) | Length (um) | Speed Mean(um/s) | Straightness |
|---|---|---|---|---|
| Y79 TRAIL-R1 + CAP | 2.51±3.2* | 4.477±4.48† | 0.012±0.0037‡ | 0.613±0.343 |
| ARPE-19 TRAIL-R1 + CAP | 1.282±2.10* | 1.841±2.34† | 0.00514±0.002† | 0.628±0.229 |
|  |  |  |  |  |
| Y79 TRAIL-R1 + Helium | 0.68±37 | 1.79±1.06 | 0.004±0.002 | 0.41±0.17 |
| ARPE-19 TRAIL-R1 + Helium | 1.85±1.43 | 2.01±1.63 | 0.1±0.001 | 0.96±0.084 |

FIG. 15

| RNS | Helium/1min | 1.6W CAP/1min | Helium/2mins | 1.6WCAP/2mins | $H_2O_2$ | No Treatment |
|---|---|---|---|---|---|---|
| Y79-Tumor Cells RNS (Green) | A | B | C | D | E | F |
| ARPE-19 Normal Cells RNS (Green) | G | H | I | J | K | L |
| % RNS Y79-Tumor Cells | 22.48±6.15 | 59.5±3.04* | 33.335±0.17 | 76.54±9.64† | 94.73±4.71 | 5.88±3.67 |
| % RNS ARPE-19 Normal Cells | 0.9±1.1 | 0.95±0.95* | 0 | 3.13±1.64† | 83.04±4.47 | 1.85±1.85 |

FIG. 17

| 1.4W CAP | % ARPE-19 Positive for Nf-κb | | % Y79 Positive for Nf-κb | |
|---|---|---|---|---|
| | Activated Nf-κb in nucleus | Cytoplasmic Nf-κb | Activated Nf-κb in nucleus | Cytoplasmic Nf-κb |
| Helium 1 min | 0 ± 1.0 | 7 ± 0.0 | 0 ± 0.0 | 1 ± 0.13 |
| Helium 2 min | 0 ± 1.0 | 5 ± 0.30 | 0 ± 0.0 | 0 ± 0.0 |
| Helium 3 min | 0 ± 1.0 | 4 ± 0.33 | 15 ± 0.73 | 0 ± 0.0 |
| 40P 1 min | 7 ± 0.33* | 100 ± 1.03 | 78 ± 1.17* | 78 ± 1.07 |
| 40P 2 min | 19 ± 0.63† | 100 ± 0.87 | 100 ± 5.77† | 0 ± 0 |
| 40P 3 min | 52 ± 1.07‡ | 98 ± 0.97 | 100 ± 1.0‡ | 0 ± 0.57 |
| $H_2O_2$ | 100 ± 0.80 | 100 ± 0.80 | 97 ± 0.67 | 100 ± 0.67 |
| No treatment | 1 ± 0.13 | 11 ± 0.6 | 0 ± 0.0 | 0 ± 0.0 |

FIG. 19

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```

```
ggattgtggc cttctttgag                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaaactgag cagagtcttc                                              20
```

SYSTEM AND METHOD FOR SELECTIVE ABLATION OF CANCER CELLS WITH COLD ATMOSPHERIC PLASMA

CROSS-REFERENCE TO RELATED APPLICATIONS

The present application is a continuation-in-part of U.S. Non-provisional Application Ser. No. 14/725,167, filed on May 29, 2015, entitled "Integrated Cold Plasma and High Frequency Plasma Electrosurgical System and Method," which claims the benefit of the filing date of U.S. Provisional Patent Application Ser. No. 62/004,360 filed on May 29, 2014.

Further, the present application claims the benefit of the filing date of U.S. Provisional Patent Application Ser. No. 62/075,638 filed by Dr. Jerome Canady and Arpitha Parthasarathy on Nov. 5, 2014.

The aforementioned provisional patent application is hereby incorporated by reference in its entirety.

STATEMENT REGARDING FEDERALLY SPONSORED RESEARCH OR DEVELOPMENT

None.

SEQUENCE LISTING

The instant application contains a Sequence Listing which has been submitted electronically in ASCII format and is hereby incorporated by reference in its entirety. Said ASCII copy, created on Dec. 8, 2015, is named 9101-034_SL.txt and is 943 bytes in size.

BACKGROUND OF THE INVENTION

Field of the Invention

The present invention relates to a systems for producing cold plasmas.

Background of the Related Art

Reactive Oxygen Species (ROS) can alter signal transduction cascades (see, S. Chakraborti and T. Chakraborti, "Oxidant-mediated activation of mitogen-activated protein kinases and nuclear transcription factors in the cardiovascular system: a brief overview," Cell Signal 1998; 10, 675-683) as well as induce changes in transcription factors that mediate immediate cellular stress responses (see, C. K. Sen and L. Packer, "Antioxidant and redox regulation of gene transcription," FASEB J. 1996 10, 709-720). Cold Atmospheric Plasma (CAP) has been known to induce cell stress and release of reactive oxygen species (ROS) in promoting cell death and apoptosis. See, Cheng X, Sherman J, Murphy W, Ratovitski E, Canady J, Keidar M. The effect of tuning cold plasma composition on glioblastoma cell viability. PLoS One. 2014; 9(5).

Several tumor cell lines have been studied to confirm that ROS is involved in triggering cell stress. See, Keidar M, Walk R, Shashurin A, Srinivasan P, Sandler A, Dasgupta S, Ravi R, Guerrero-Preston R, Trink B. Cold plasma selectivity and the possibility of a paradigm shift in cancer therapy. Br J Cancer. 2011; 105(9):1295-301. However, the down-stream signaling mechanisms, the molecules at the cell surface and receptors involved have not been well studied. Although TNF has been associated in breast cancer ad a potential therapeutic target, specific receptor targets of TNF is gaining more importance. See, F. Balkwill, "TNF-alpha in promotion and progression of cancer," Cancer Metastasis Rev. 2006; 25(3):409-16. Because of TRAIL-R1 profile has high tumor specificity when compared to other TNF family members, recombinant soluble TRAIL and agonistic antibodies against its receptors are actively being developed for clinical cancer therapy. See, Grunert M, Gottschalk K, Kapahnke J, Giindisch S, Kieser A, Jeremias I., "The adaptor protein FADD and the initiator caspase-8 mediate activation of NF-κB by TRAIL," Cell Death Dis. 2012; 3:e414.

Molecular mechanisms of TRAIL-R1 activation by NF-kB through death rector DR4 domain are known to recruit caspase 8. DR4 receptor depends on activation of caspases as well as of lysosomal activity. Furthermore, TRAIL and cancer stem cell phenotype observed in breast tumor spheroids show an upregulation of cyclooxygenase-2 (COX-2) pathway. See, Chandrasekaran S, Marshall J R, Messing J A, Hsu J W, King M R., "TRAIL-Mediated Apoptosis in Breast Cancer Cells Cultured as 3D Spheroids," PLoS One. 2014; 9(10):e111487.

The unique chemical and physical properties of cold atmospheric plasmas ("CAP") enable their numerous recent applications in biomedicine including sterilization, the preparation of polymer materials for medical procedures, wound healing, tissue or cellular removal and dental drills. A. Fridman, Plasma Chemistry (Cambridge University Press, 2008); G. Fridman, G. Friedman, A. Gutsol, A. B. Shekhter, V. N. Vasilets, and A. Fridman "Applied Plasma Medicine", *Plasma Processes Polym.* 5, 503 (2008); E. Stoffels, Y. Sakiyama, and D. B. Graves "Cold Atmospheric Plasma: Charged Species and Their Interactions With Cells and Tissues" *IEEE Trans. Plasma Sci.* 36, 1441 (2008); X. Lu, Y. Cao, P. Yang, Q. Xiong, Z. Xiong, Y. Xian, and Y. Pan "An RC Plasma Device for Sterilization of Root Canal of Teeth" *IEEE Trans. Plasma Sci.* 37, 668 (2009).

Plasma-based nitrogen oxide (NO) therapy demonstrated huge potential for stimulation of regenerative processes and wound healing. The work uncovering function of nitrogen oxide as a signal molecule was awarded by the Nobel Prize in medicine and biology in 1999. NO-therapy demonstrated tremendous effect of acceleration of healing of ulcer, burns and serious wounds. Other experimental evidence supports efficiency of cold plasmas produced by dielectric barrier discharge for apoptosis of melanoma cancer cell lines, treatment of cutaneous leishmaniasis, ulcerous eyelid wounds, corneal infections, sterilization of dental cavities, skin regeneration, etc.

Recent progress in atmospheric plasmas led to creation of cold plasmas with ion temperatures close to room temperature. Cold non-thermal atmospheric plasmas can have tremendous applications in biomedical technology. K. H. Becker, K. H. Shoenbach and J. G. Eden "Microplasma and applications" *J. Phys. D.: Appl. Phys.* 39, R55-R70 (2006). In particular, plasma treatment can potentially offer a minimum-invasive surgery that allows specific cell removal without influencing the whole tissue. Conventional laser surgery is based on thermal interaction and leads to accidental cell death i.e. necrosis and may cause permanent tissue damage. In contrast, non-thermal plasma interaction with tissue may allow specific cell removal without necrosis. In particular, these interactions include cell detachment without affecting cell viability, controllable cell death etc. It can be used also for cosmetic methods of regenerating the reticular architecture of the dermis. The aim of plasma interaction with tissue is not to denaturate the tissue but rather to operate under the threshold of thermal damage and to induce chemically specific response or modification. In particular presence of the plasma can promote chemical reaction that would have desired effect. Chemical reaction can be promoted by tuning the pressure, gas composition and energy. Thus the important issues are to find conditions that produce effect on tissue without thermal treatment. Overall plasma treatment offers the advantage that is can never be thought of in most advanced laser surgery. E. Stoffels, I. E Kieft, R. E. J Sladek, L. J. M van den Bedem, E. P van der Laan, M. Steinbuch "Plasma needle for in vivo medical treatment: recent developments and perspectives" *Plasma Sources Sci. Technol.* 15, S169-S180 (2006).

In recent few years cold plasma interaction with tissues becomes very active research topic due to aforementioned potential. Preliminary experiments have demonstrated potent effects of cold plasma treatment on cancerous tissue both in vitro and in vivo and suggest the important role of the reactive oxygen species (ROS) in the selective treatment of cancer. In-vivo efficiency of cold plasmas for ablation of mid-sized subcutaneous bladder cancer tumors on mice was demonstrated. M. Keidar, A. Shashurin, R. Ravi, R. Guerrero-Preston and B. Trink, *British Journal of Cancer* 105, 1295 (2011). Also, selectivity of plasmas for killing of cancerous cells while remaining healthy cells intact was demonstrated in vitro for various cell lines. Cellular level effects include detachment of cells from extracellular matrix and decreasing of migration velocity of cells, while the sub-cellular level effect is the reduction of cell surface integrin expression (receptors responsible for cell adhesion and migration). A. Shashurin, M. Keidar, S. Bronnikov, R. A. Jurjus, M. A. Stepp, *Appl. Phys. Let.* 92, 181501 (2008). A. Shashurin, M. A. Stepp, T. S. Hawley, S. Pal-Ghosh, L. Brieda, S. Bronnikov, R. A. Jurjus, M. Keidar, Influence of cold plasma atmospheric jet on integrin activity of living cells *Plasma Process. Polym.* 7 294 (2010). In addition, it was found that normal and cancer cells respond to CAP differently depending on the where they are in terms of the cell cycle through their various life functions. Migration of normal cells was reduced by 30% (p<0.001), however the cancer cells react differently: more aggressive carcinoma cells showed more response in the decrease of the migration rates (~20% with p<0.001) than less aggressive papilloma cells (p>0.05). It was also found that CAP induces a transient 2-fold G2/M-arrest in papilloma and carcinoma cells; normal epithelial cells did not show any change in cell cycle progression. O. Volotskova, T. S. Hawley, M. A. Stepp & M. Keidar, "Targeting the cancer cell cycle by cold atmospheric plasma," *Scientific Reports*, 2:636, Sep. 6, 2012

Given these findings, cold plasma represents a promising new adjunct for cancer therapy, offering the ability to directly target and selectively kill cancerous cells. CAP can lead to a new paradigm in cancer therapy by offering a minimum-invasive surgery technique that allows specific cell removal without affecting the whole tissue. CAP demonstrated in-vitro and in-vivo highly selective potential towards number of cancer cell line (lung, bladder, head & neck, skin etc.) and, as such, has potential to address limitations of current clinical chemotherapeutic approaches contain with regards to nonselective and incomplete tumor ablation. In addition, CAP action leads to selective decrease in cancer cell migration, thus has potential to mitigate the metastasis and may lead to the development of a novel therapeutic approach for metastasis.

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in WO 2012/061535 A2, which disclosed a system for simultaneously cutting and coagulating tissue.

SUMMARY OF THE INVENTION

The present invention relates to the system comprised of two units namely Conversion Unit (CU) and Cold Plasma Probe (CPP). The CU is connected to an electrosurgical generator (ESU) output and does conversion of the ESU signal. The CPP is connected to the CU output. At the end of the CPP cold plasma is produced and is thermally harmless to living tissue, i.e., it cannot cause burns to the tissue.

Although cold atmospheric plasma (CAP) has been suggested to induce apoptosis, the mechanism of action and the pathways involved previously have not well defined. An altered redox potential due to reactive oxygen species (ROS) mediates cell death in various tumors in the presence of CAP. In the present invention, the signaling molecule at the cell surface that is activated by CAP is identified, a novel identity to plasma medicine that may trigger the downstream NF-kB apoptotic cascade. Besides inducing apoptosis, the present invention identifies the involvement of a new receptor in plasma medicine, a Tumor necrosis factor (TNF)-related apoptosis-inducing ligand (TRAIL). TRAIL receptor 1 (TRAIL R-1) activates apoptosis through the death receptors DR4 and DR5. In breast cancer epithelial cells, TRAIL-R1 expression was elevated when treated with CAP along with a concomitant release of ROS in majority of the breast cancer cells as opposed to the unaltered normal breast epithelial cells. This is the first report to identify the specific receptor that is involved in triggering cell death through CAP using the cold plasma s of the present invention. Our results show that signaling first starts by triggering TRAIL R-1 within one minute of treatment with CAP inducing ROS release through mitochondria. Mitochondrial ROS positive, superoxide positive cells were all positive to higher expression of TRAIL R-1. We also confirm that cell stress and superoxide release is specific to ROS and not Reactive Nitrogen Species (RNS). We have identified in the current study a novel mechanism by which plasma induces mitochondrial cell stress inducing higher levels of TRAIL R-1 expression in breast cancer, which has immediate applications in plasma therapeutics and regenerative medicine.

In a preferred embodiment the present invention is a method for elevating a TRAIL-R1 expression in cancer cells to induce apoptosis. The method comprises the steps of receiving electrical energy having a specific voltage, frequency and power from an electrosurgical generator, up-converting the voltage and down-converting the frequency with a high voltage transformer having a primary coil and a secondary coil, the secondary coil having a larger number of turns than the primary coil, applying said converted electrical energy to an electrode in an electrosurgical hand piece, flowing an inert gas through said electrosurgical hand piece to produce a cold plasma at a distal end of said electrosurgical hand piece; and applying said cold plasma to cancer cells for 1 to 3 minutes. The inert gas may comprise, for example, helium or argon. In a preferred embodiment the cold plasma is applied to cancer cells for about 2 minutes.

It is an object of the invention to provide a system for producing cold plasma. The system includes Conversion Unit and Cold Plasma Probe.

CU is connected directly to an electrosurgical unit. The CPP is connected to the CU output. Cold plasma is produced at the distal end of the CPP. The connection schematics are shown in FIG. 1.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE FIGURES

For a more complete understanding of the present invention and the advantages thereof, reference is now made to the following description and the accompanying drawings, in which:

FIG. 11 is a table demonstrating the percentage of the total number of Apoptotic cells double positive for mitosox and TRAIL R-1 in Example 2 below. Significant number of cells (*$p \leq 0.05$ N=100 from two independent experiments) are double positive suggesting apoptotic cells are more after plasma treatment only in breast cancer cell line and such cells are absent in the normal cell line.

FIG. 12 is a table showing a viability test after CAP Treatments. A time course assay with CAP on retinoblastoma and normal epithelial cells showed selective response to cell death. Significant (*$p \leq 0.001$) increase in cell death was observed in the Y-79 cells at 1 minute and 2 minute treatments with CAP with less than 34% cell death in Helium. Positive control $H_2O_2$, an oxidative cell stress inducer showed almost 100% cell death and this pattern was absent in the untreated normal and tumor cells. Note the APRE-19 normal cells showing negligible effect due to CAP.

FIG. 13 is a table illustrating apoptosis induced with CAP in Retinoblastoma showing TUNEL positive cells. Y-79 cells in presence of CAP for 2 minutes show significant increase in apoptosis by inducing DNA nick (B; green positive nuclei cells-arrow) than the normal ARPE-19 cells (F-J) (*$p \leq 0.001$). Note the absence of TUNEL positive cells in Helium and untreated treatment, while the positive controls $H_2O_2$ and TNF-α showed significant apoptosis in Y-79 cells (A, C-E). DAPI counter stained nuclei (blue). Scale bar 10 μm.

FIG. 15 is a table illustrating Endocytotic recycling of TRAIL-R1 analyzed by TIRF microscopy. The endocytotic vesical trafficking of TRAIL-R1 was recorded in the EGFP transfected cells. Live cell imaging with TIRF images was analyzed for the speed, distance, tortuous displacement after CAP treatment in Y-79 and ARPE-cells. CAP treated retinoblastoma cells showed increased recruitment of TRAIL-R1 at the cells surface along with increase in speed, length and tortuous movement of the vesicles containing TRAIL-R1 particles (*p≤0.05). This pattern of vesicle internalization was absent in the normal ARPE cells and cells treated with helium.

FIG. 17 is a table showing detection of RNS mediated mitochondrial cells stress in the presence of CAP. The % of cells showing RNS positivity was significantly increased upon CAP treatment for 1 or 2 minutes (60-70%) in Y-79 cells (Arrows-Green; B, D). These cells showed similar pattern of intracellular RNS positive cells to as that of the ROS (50 to 60% positive cells; FIG. 3), suggesting that both intracellular ROS and RNS mediated mitochondrial cells stress is involved. Note the presence of RNS positive ARPE-19 cells in $H_2O_2$ treated group and the absence of RNS positive cells in CAP treated ARPR-19. DAPI counter stained nuclei (blue). Scale bar 10 μm

FIG. 19 is a table showing percentage of cells positive for NF-κB p65 activity 48 hrs after CAP treatments. The optimal condition for activation was determined by translocation of NF-κB p65 from cytoplasm to nucleus. Helium treatment in both ARPE-19 and Y79 cells showed negligible NF-κB activity. Within 1 minute of CAP there was significant activation of NF-κB activity in Y79 when compared to ARPE-19 (*P≤0.05). A significant increase (†p≤0.05) of almost 100±5.77% nuclear localization was observed in the Y79 cells with CAP treatment when compared to 19±0.63% in the ARPE-19 cells after 2 minutes of treatments. Increase in treatment time to 3 minutes (‡p≤0.05) showed a shift towards the nucleus even in the ARPE-19 (52±1.07%), suggesting that 2 minute treatment was most optimal for Y79 cells.

DETAILED DESCRIPTION OF THE PREFERRED EMBODIMENT

Figure 1:
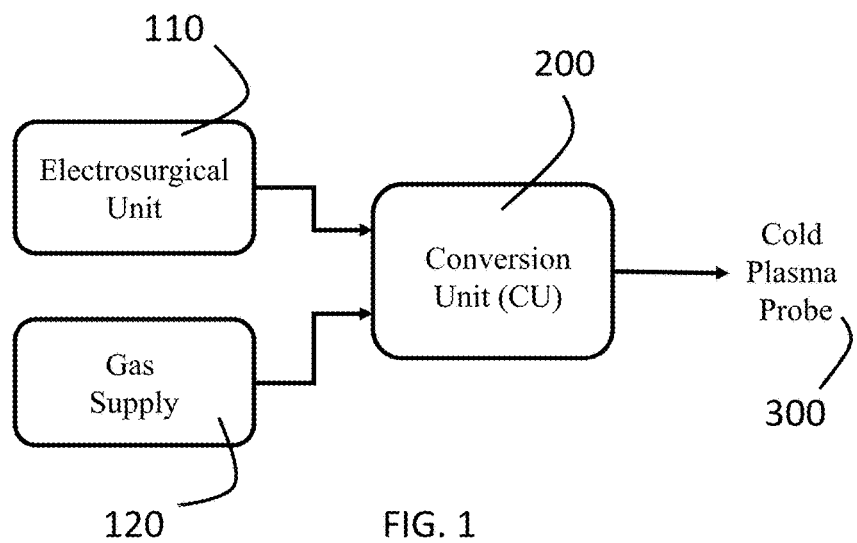
FIG. 1 is a diagram of a system for producing cold plasmas in accordance with a preferred embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. The preferred embodiment of the invention is described for illustrative purposes, it being understood that the invention may be embodied in other forms not specifically shown in the drawings.

The present invention produces cold plasmas which are thermally harmless for the living biological tissue and cannot cause burns. The cold plasma produced by the present invention, however, is deadly for cancer cells while leaving normal cells unaffected.

Figure 2:
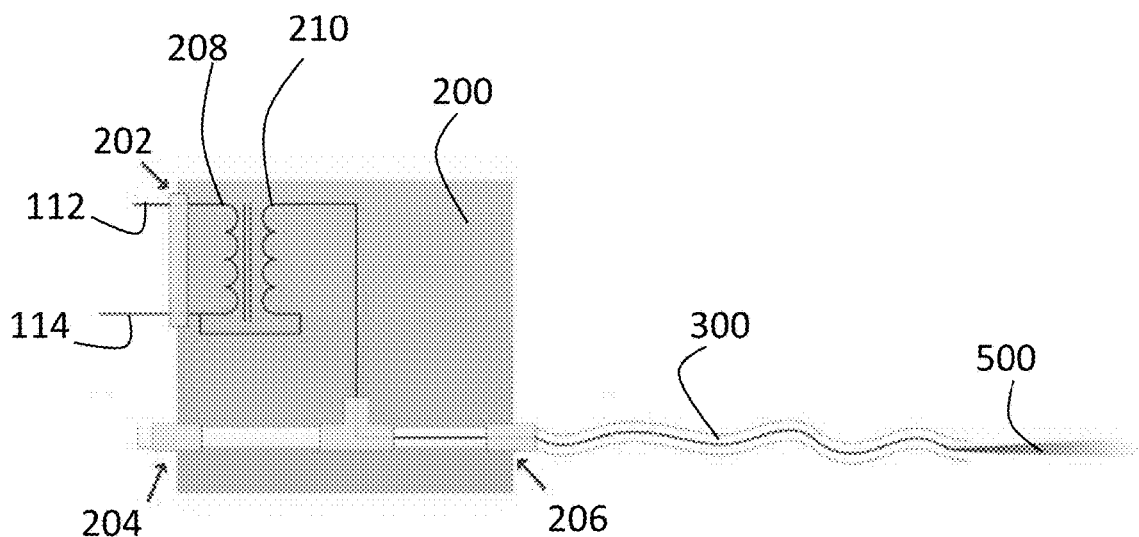
FIG. 2 is a diagram of a Conversion Unit (CU) and Cold Plasma Probe (CPP) in accordance with a preferred embodiment of the present invention.

The conversion unit (CU) 200 is equipped with 3 connectors, namely a gas connector 204 (to helium tank 120), an electrical connector 202 (to electrosurgical unit 110) and an electro-gas connector 206 (to cold plasma probe 300) as shown in FIG. 2.

The gas connector 204 is an input connection. It connects an inert gas such as Helium tank 120 to the CU 200 and delivers the inert gas to the CU. For example, different grades of the Helium can be used to the helium tank. Flow rates less than 1-15 L/min should be used.

The electrical connector 202 is an input connection. It connects between the ESU 110 and the CU 200 and delivers power to the CU 200. A high voltage output 112 of the ESU and a patient output 114 of the ESU 110 are used as inputs to the CU 200.

The electro-gas connector 206 is the output of the CU 200 and is connected to the cold plasma probe (CPP) 300. The electro-gas connector 206 supplies an output electrical signal and helium to the cold plasma probe.

Figure 3A:
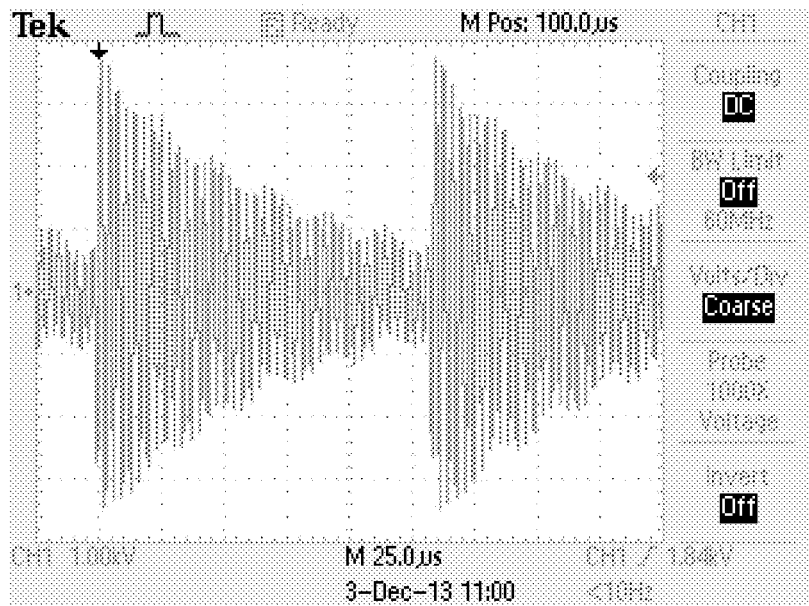
FIGS. 3A and 3B show converted waveforms output from a CU in accordance with a preferred embodiment of the present invention.
Figure 3B:
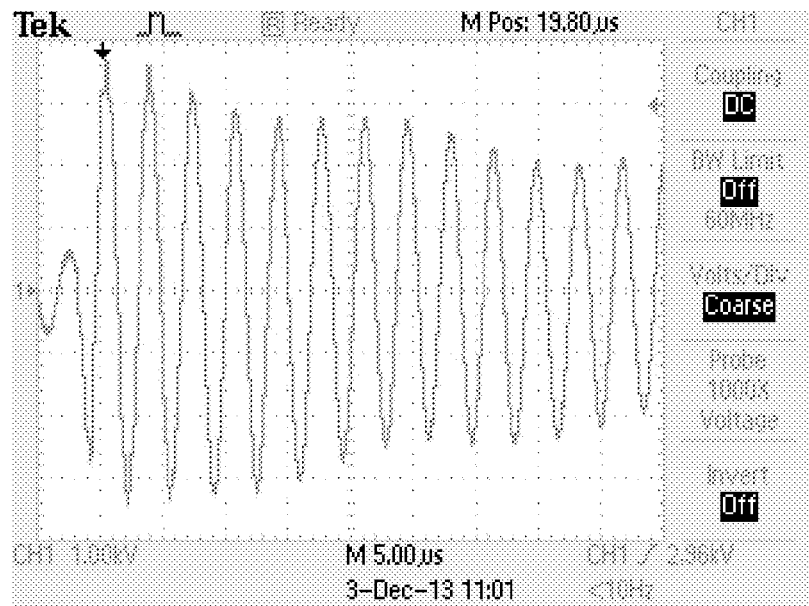

The CU 200 utilizes a high voltage transformer connected to output from ESU 110 as shown in FIG. 2. In a preferred embodiment, the transformer utilizes a primary coil 208 with $N_1$=60-70 turns and secondary coil 210 with about $N_2$=300 turns. The coils are wound on a ferrite core. The specific number of turns utilized in the transformer is given for illustrative purpose only and can be varied in a very wide range. The number $N_2$ should be larger than $N_1$ in order to produce step-up conversion of the voltage. The CU output waveform in the preferred embodiment is shown in FIG. 3.

The CU up-converts voltage. In the preferred embodiment voltage of about 4 kV is produced. Other embodiments of the CU can be used to up-convert the voltage. The output voltage of the CU should be in a range 1.5-50 kV.

The CU down-converts frequency. In the preferred embodiment frequency about 295 kHz is produced. Other embodiments of the CU can be used to down-convert the frequency. Outputted frequencies should be less than about 300 kHz.

The CU down-converts power. In the preferred embodiment, secondary coil can produce power <10 Watt. Other embodiments of the CU can be used to down-convert the frequency. The CU output power should not exceed 20-30 Watt.

A Cold Plasma Probe (CPP) 300 is connected to Electro-Gas output connector 206 of the CU. Probe length was about 0.5 meter in the preferred embodiment. However, the present invention is not limited solely to this CPP length, and probe can be up to 5-10 meters long. Output voltage of the transformer should be increased if longer probes are used.

The Cold Plasma Probe 300 is made of flexible tube and equipped with wire electrode. The probe 300 may have at its distal end a housing or other structure 310 for use in holding the distal end of the probe. Other structures such as handle may be used but are not necessary. Wire electrode in the preferred embodiment is located inside the tube. However, it can also be placed outside the tube.

The cold plasma 500 is triggered, for example, by pressing the foot pedal in Coagulation mode. Any Coagulation powers can be used, however increase of the Coagulation Power setting will result in brighter and more intense cold plasma In the preferred embodiment, CPP has no control buttons on it and cold plasma is turned on directly by pressing the foot pedal. However, CPP may be equipped with control buttons in order to ignite cold plasma and adjust helium flow by pressing buttons on the CPP itself.

Figure 5A:
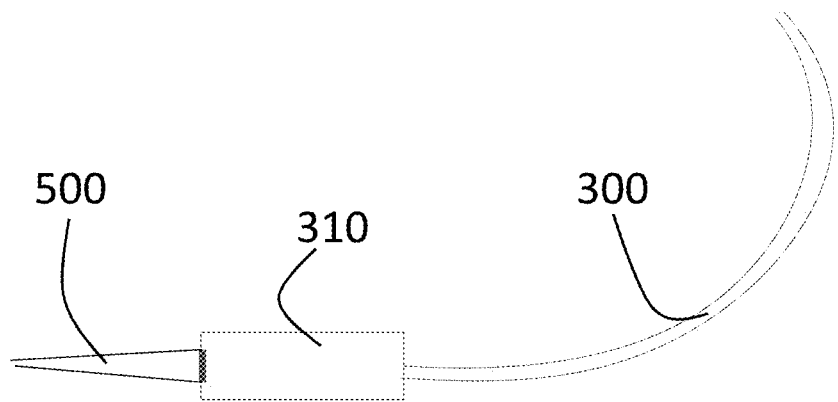
FIG. 5A is an illustration of free cold plasma generated in accordance with a preferred embodiment of the present invention.
Figure 5B:
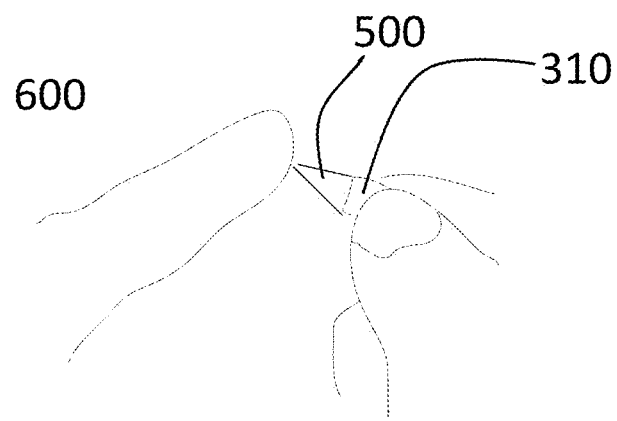
FIG. 5B is an illustration a cold plasma generated in accordance with a preferred embodiment of the present invention in contact with finger.
Figure 6:
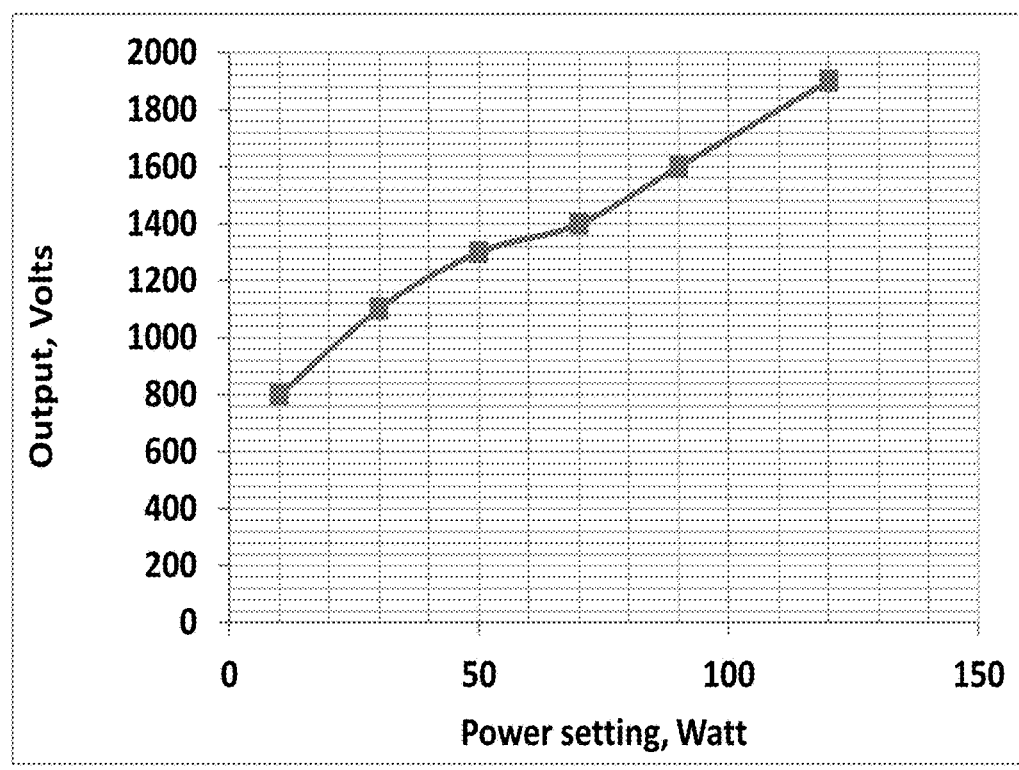
FIG. 6 is a graph of RMS output voltage of Conversion Unit vs. input power setting on an electrosurgical unit (ESU) unit.

The length of free cold plasma jet in experiments was up to 3-4 cm as shown in FIG. 5A. Placing finger into the cold plasma without any damage is shown in FIG. 5B.

EXAMPLE 1

The transformer in the CU utilizes primary coil with N1=30 turns of AWG 30 magnet wire and secondary coil with about N2=250 turns of AWG 36 magnet wire. Ferroxcube core UR64/40/20-3C90 was used. Insulation between the windings was up to 10 kV and between the windings to the core—up to 7 kV.

The Conversion Unit in this embodiment produced high voltage with RMS up to about 2 kV and frequency about 150 kHz. Power delivered into cold plasmas was <5 Watt. The dependence of RMS output voltage of Conversion Box vs. input power setting on ESU is show in FIG. 2.

Figure 8:
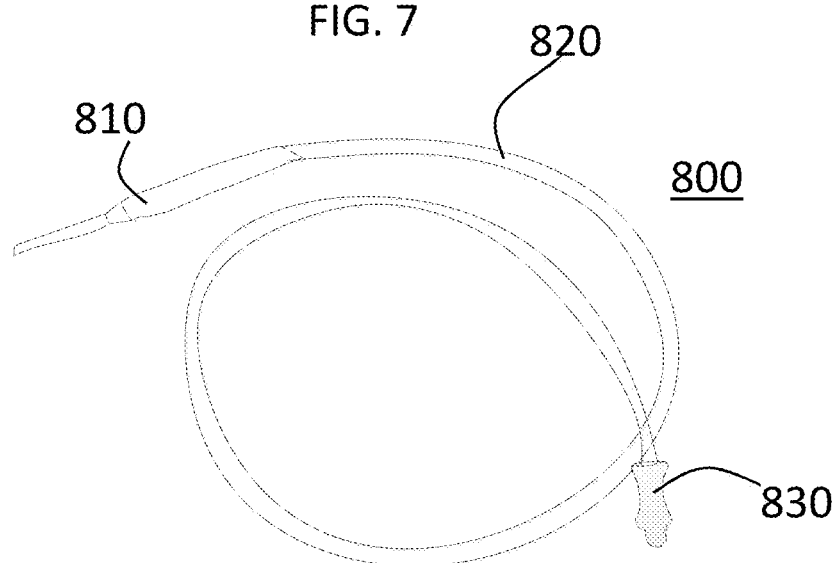
FIG. 8 is a schematic diagram of a Cold Plasma Probe (CPP) in accordance with another preferred embodiment of the present invention.
Figure 9:
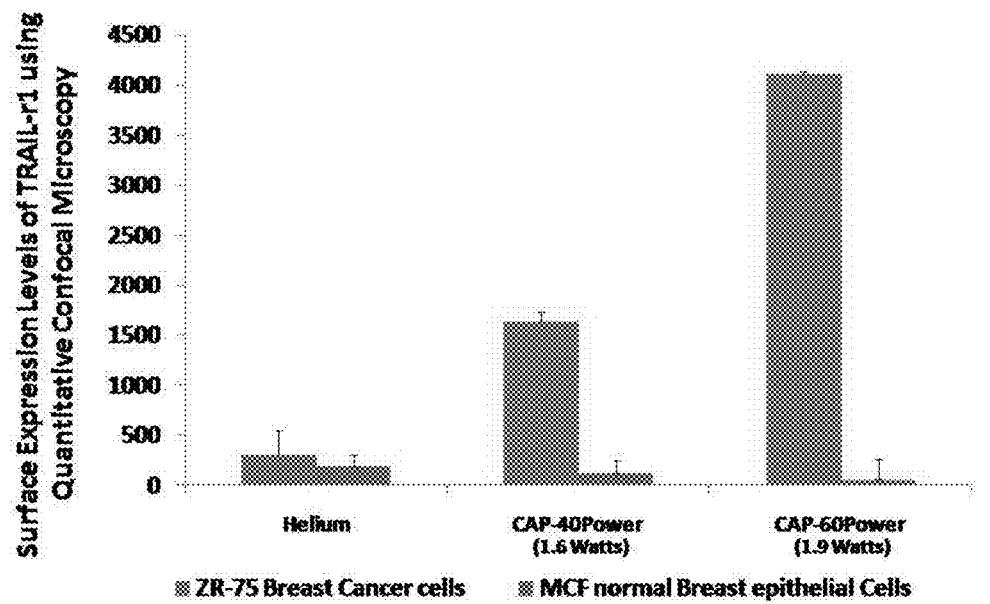
FIG. 9 is a bar graph of quantitative confocal microscopy for expression levels of TRAIL R-1. Z-stack images from Example 2 below were quantified for surface expression. The graph shows high expression levels of TRAIL-R1 after treatments with plasma at 1.6 W and 1.9 Watts for one minute when compared to helium alone, $p \leq 0.05$ N=100 from two independent experiments.
Figure 10:
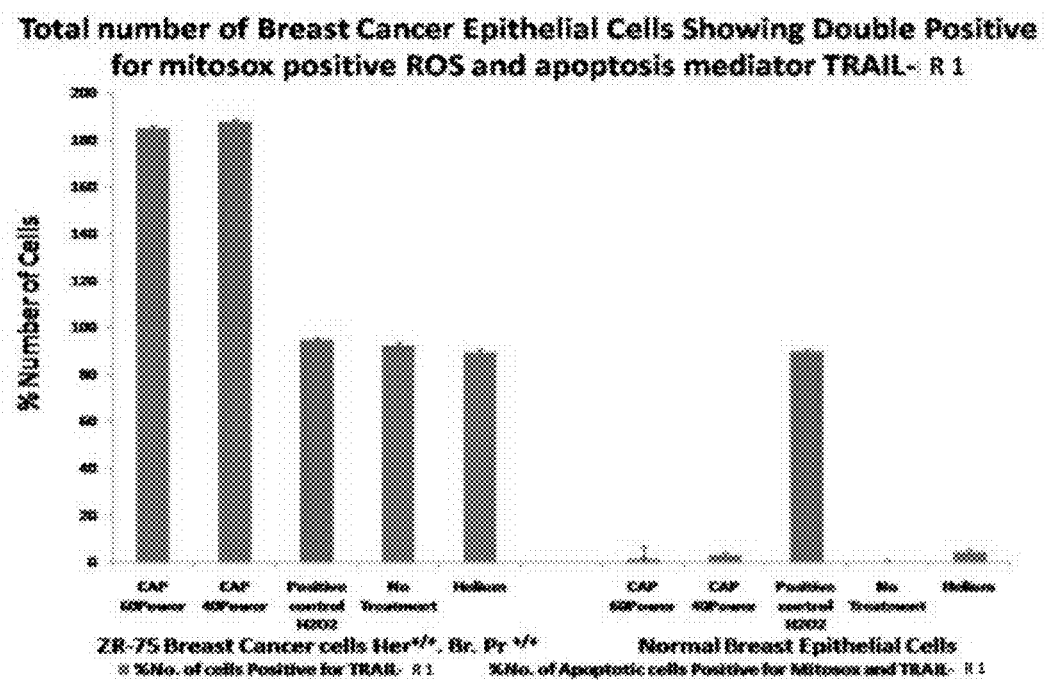
FIG. 10 is a bar graph of the percent of total number of cells showing Mitochondrial Cell stress induced apoptosis through TRAIL-R1 in Example 2 below. The graph shows a significant difference in the apoptosis between cancer cells and normal cells. Total number cells positive for apoptosis was indicated with double positive cells for ROS (mitosox positive cells) and TRAIL-R1 (FIG. 1) with CAP treatments at 40 and 60 power settings. H2O2 a positive control showed 100% positive for ROS. ZR-75-1 cells was significantly going through apoptosis when compared to cells treated with helium. $p \leq 0.05$ N=100 from two independent experiments.

CPP shown in FIG. 8 can utilize one-electrode or two-electrode configuration. In one-electrode configuration—high voltage electrode can be placed inside the flexible tube used for the Helium supply or embedded in the tube's wall. In two-electrode configuration high voltage electrode is placed inside the tube and grounded shield is embedded in the tube walls.

Figure 7:
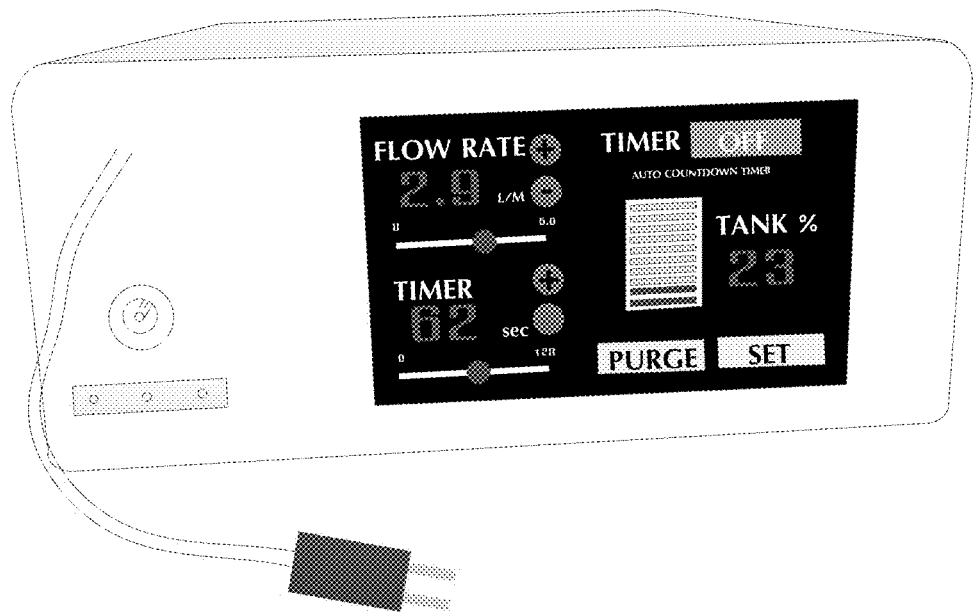
FIG. 7 is a diagram of a Conversion Unit in accordance with another preferred embodiment of the present invention.

The schematic view of the Conversion Box and 3 meter long Cold Plasma Probe are shown in FIGS. 7 and 8 respectively. Preferred Helium flow rate for this embodiment was about 5 LPM. The probe 800 has handle 810, an elongated tube 820 and a connector 830 for connecting the probe to the CU.

EXAMPLE 2

Cell Culture.

The human ZR-75-1 Breast Cancer Her2+, Er+, Pr+ epithelial cell line (referred as ZR-75 in the article) was cultured at 37° C. in 5% $CO_2$ in a RPMI medium, supplemented with heat inactivated 10% fetal bovine serum and with 5% penicillin-streptomycin and gentamycin (Sigma Aldrich, MO). MCF-12 normal Breast epithelial cell line (referred as MCF in the article) was cultured using 1:1 DMEM and Ham's F12, 20 ng/ml HGF, 100 ng/ml cholera toxin, 0.01 mg/ml Bovine Insulin, 500 ng/ml hydrocortisone, 5% of 95% horse serum (Sigma Aldrich, MO). The cell lines were purchased from (American Type Culture Collection, Manassas, Va.). The coverglass 24 well plates were coated with fibronectin for 30 minutes before seeding the cells onto the plates. Cells were seeded at a density of $1 \times 10^5$ cells/well in 24-well plastic cell culture plates and used at ~40% confluence, as determined by Zeiss phase-contrast microscopy.

Cold Atmospheric Plasma Treatment.

The multiwall plate was placed on a multi-therm shaker to maintain cultures at 37° C. CHCPS was fixed stationary to the arm and the multiwall plate was subjected to 200 revolutions per minute during treatment with CAP. CAP treatments were performed using the generator box coupled with a cold plasma converter box to have power setting output of either, 40 power setting (1.6 Watts), 60 power settings (1.9 Watts) over a period of one minute and control treatments with helium. All experiments were carried out as per BSL2 certified requirements in a Biosafety Cabinet.

Note the 24 well-plate was placed in a multi-therm shaker to maintain 37° C. in a biosafety hood during the course of the CAP treatment of epithelial cells (A). Arrow-Showing Hand piece of Canady Helios™ Cold Plasma Scalpel (A) The entire set up with the SS-601MCa Canady Plasma. Electrosurgical System and the converter box (black) for cold plasma connected to the experimental set up also showing the foot pad and helium source. Note the enlarged image of the SS-601MCa generator and the converter box. Labeling of Mitochondria and Detection of Mitochondrial Superoxide.

Mitochondria were visualized using the fluorescent dye for specific analysis of mitochondrial production of superoxide, the cell-permeable MitoSOX Red reagent was used (Invitrogen). MitoSOX Red selectively targets mitochondria and fluoresces when rapidly oxidized by superoxide (excitation at 510 nm, emission at 580 nm). Y75 breast cancer cells and MCF-12 normal Breast epithelial cells ($1 \times 10^5$ cells)) were seeded onto glass bottom—multiwall plates (Matek Corp) and cultured until ~30% confluent in 24-well plates. After treatment with CAP using Canady Hybrid Plasma Scalpel at 40 power setting (1.6 Watts), 60 power settings (1.9 Watts) or one hour treatment with Hydrogen Peroxide 10 uM at 37° C., cells were washed twice in medium and coincubated with 5 μM MitoSOX Red, for 20 min at 37° C. in the dark.

After washes in medium, the coverglass dishes were fixed in −20° C. cold methanol for 10 minutes and preceded for immunostaining with TRAIL R-1. Coverslips were mounted on slides and stored in the dark at 4° C. prior to examination. The degree and pattern of fluorescence were determined using an Zeiss SD microscope. Images were captured using a ×63 oil immersion objective and Zen software. Identical conditions and exposure times were used in each experiment and set to avoid overexposure of the MitoSOX Red. The degree of fluorescence was assessed in a blinded fashion, with cancer cells imaged first and the same settings were used for control normal cells.

Immunostaining for TRAIL-R1 and Quantitative Confocal Microscopy.

We developed a method to stain TRAIL-R1 immunostaining and method to quantify the surface labelling of TRAIL-R1 expression on isolated epithelial cells. TRAIL-R1 antibody was applied to the fixed cells at dilution of 1:10 (Santa Cruz, Calif.) for one hour after blocking with 5% BSA in phosphate buffered saline (PBS) (1 hr at room temperature). Secondary antibody anti mouse IgG Alexa 488 (Molecular Probes, life technologies, NY) was applied at 1:250. Cells were washed in PBS after one hour incubation. Appropriate isotype controls (Invitrogen, NY) were used. Cells were counterstained with mounting medium containing DAPI (Vector Laboratories, CA). Zeiss spinning Disc images along the Z-stack was acquired with the same exposure settings for cancer and normal cells. An overlay image was created along with the transmitted light and quantified for total protein expression on each cell. Polygon tool was used to draw an ROI (region of interest) along the cell surface of the 2D reconstructed images for TRAIL-R1 using Zen software. The expression levels were recorded in an excel file to track the cells for mitosox positivity and count the total number of single and double positive cells.

Data Presentation and Statistical Analysis.

Data for percentage of total cell number and expression levels for TRAIL R-1 are presented as means±SD; n represents the number of individual epithelial cells from a specified number of experiments. Data generated from captured images of ROS-induced fluorescence were assessed by counting the number of double positive cells and total number of cells per field. Data are presented as total protein expression normalized against the background untreated cells or against cells stained with isotype control using Zeiss confocal Zen software. The background was normalized for all cells quantified for fluorescence expression. For statistical analysis, pair-wise comparisons Kruskal-Wallis one-way ANOVA and Non parametric analysis with Manwhitney U test were performed. A statistically significant difference was accepted at $P<0.05$.

EXAMPLE 3

Immortalized Human RPE (ARPE-19) and Y-79 retinoblastoma cells were purchased from American Type Culture Collection (ATCC, Manassas, Va., USA), cultured and propagated in Dulbecco's Modified Eagles Medium or RPMI-1640 (DMEM; Invitrogen-Gibco, Life Technologies, Long Island, N.Y., USA) respectively. The medium contained 10% FBS for ARPE-19 and 20% FBS for Y-79 (Sigma Aldrich, St Louis, Mo., USA), 100 IU/ml penicillin-streptomycin, 50 ug/ml gentamycin (Invitrogen-Gibco, Life Technologies, Long Island, N.Y., USA). The cells were incubated in a humidified atmosphere of 5% $CO_2$ and 95% air at 37° C. Positive controls used in the study included treating cells with $H_2O_2$ and TNF-α. $H_2O_2$ was added at 5 mM concentration and incubated for one hour and 200 ng/ml of TNF-α was incubated for 24 hrs in culture. $H_2O_2$ is a well-known oxidative stress inducer and was used as a ROS control in the entire study. For immunostaining the multiwall dishes were coated with extracellular matrix. To prepare the 24-well or 8-well glass chamber slides for imaging (Biobasic, Ontario, Canada), the Y-79 cells were coated with fibronectin and poly-D-lysine at 37° C. for 30 minutes. The extracellular matrix was removed and the cells were seeded at $2.5\times10^5$(Bio-Rad Cell counter, Hercules, Calif.) cells per well.

Cold Plasma Treatment and Experimental Set Up

The cold plasma treatments for all the cell lines were carried out in the biosafety cabinet. Twenty-four hours post seeding of cells, CAP treatments was performed. The 24 well-plate placed in a multi-thermal shaker to maintain 37° C. in a biosafety hood with the hand piece of a CAP scalpel placed inside the hood during the course of the CAP treatment of epithelial cells. Helium gas was the source for cold plasma. Other inert gases such as argon may be used. The entire set up with the SS-601MCa Canady Plasma Electrosurgical System and the converter box for cold plasma was connected to the experimental set up showing the foot pad. The cells in the multi-well chambers were treated with Cold Plasma with a beam of length of 2 cm at 1.4 W for 5 sec, 30 sec, 60 sec, 120 Sec and 180 secs in the thermal shaker to maintain 37° C. inside the hood. The same time points were maintained for Helium gas, which served as control for CAP treatments. The cultures were processed for viability test or for isolation of protein or mRNA after 48 hrs of CAP treatment or for immunoassays immediately after CAP and post 48 hr treatment.

Trypan Blue Viability Assay

Cell cultures treated with the above variables with CAP, Helium or negative control (no-treatment) and positive control $H_2O_2$ was tested for viability using trypan blue (Sigma Aldrich, St. Louis, Mo., USA). Trypan blue was added to the medium in at a proportion of 1:1 and several images were captured. Approximately 100 ARPE-19 cells from each experiment (n=3) were counted to confirm the % of cell viability. For Y-79 suspension cells, hemocytometer was used determine the % of cell viability.

TUNEL Assay for Detection of Apoptosis

Forty-eight hours after CAP treatment Apoptotic cells along with the controls was detected by terminal deoxynucleotidyl transferase (TdT)-mediated dUTP nick end labelling (TUNEL) kit (R&D Minneapolis, Minn., USA). Fifty to one hundred cells from each experiment (n=3) was analyzed using confocal Z-stack images and the % mean of TUNEL positive cells was determined for each variable.

Intracellular ROS and RNS

CAP treated ARPE-19 and Y-79 cells were subjected to further treatment with MitoSOX™ (mitosox) red as per manufacturer's instructions (Life Technologies, Long Island, N.Y., USA) for 15 minutes at 37° C. in 5% $CO_2$ to identify mitochondrial cell stress. The cultures were washed with complete medium followed by wash in phosphate buffered saline (PBS) before fixing in ice cold (–20° C.) methanol for 10 minutes. Intracellular mitosox red positive cells were detected at 510/580 nm using confocal microscopy. Some cultures were subjected to nitric oxide radical activity test to detect for intracellular RNS. CAP and helium treated cells, negative control (no-treatment) and positive controls with $H_2O_2$ were incubated with 5 μM concentration of 2',7'-difluorofluorescein diacetate, Diaminofluorescein-FM diacetate cells per manufacturer's instructions for 60 minutes at 37° C. in 5% $CO_2$. Cells were washed and fixed as described above and analyzed at detection range of 495/515 nm using confocal microscopy.

Immunostaining and Quantitative Confocal Microscopy

All the cultures in as described above were fixed in ice cold (–20° C.) methanol for 10 minutes, washed in PBS and blocked in 5% bovine serum albumin for 1 hour before incubating with the primary antibodies namely, mouse anti human TRAIL-R1 (1:10) (Santa Cruz Biotechnology, Dallas, Tex.) or rabbit anti human NF-κB (1:250) (Cell Signaling Technology, Beverly, Mass.). Isotype controls for the primary antibody were maintained. Slides were mounted with DAPI containing Vectashield mounting medium (Vector Laboratories, Burlingame, Calif.). 1 μm thick optical sections of Z-stack images were acquired using a Zeiss cell Observer Spinning Disc microscope (Carl Zeiss, Oberkochen, Germany). All the parameters were adjusted using samples treated with $H_2O_2$ to set the threshold levels of laser power, gain and exposure time for the photometric Evolve 512EMCCD camera acquisition for each of the antigen detected. These parameters were used for confocal imaging the entire time course experiments with CAP along with the specific controls. The Z-stack images were compressed to a 2D image using ZEN software and processed for total surface quantification of TRAIL-R1 using IMARIS x64 8.0.2 software. The total mean intensity was measured for each cell and about 50-100 cells in each experiment (n=3) were quantified. A threshold of mean intensity for cells in the image was measured to obtain the total surface expression of TRAIL-R1 in Y-79 and ARPE-19 cells.

Total Internal Reflection Microscopy (TIRF)

Y-79 retinoblastoma and ARPE-19 normal epithelial cells were seeded in a special TIRF Cover glass slides (Biobasic, Ontario, Canada) and transfected with 1 μg of C-Flag+IRES-eGFP (TRAIL-R1) expression vector (Genecopoeia, Rockville, Md. USA and Biobasic, Ontario, Canada), using lipofectamine (Life Technologies, Long Island, N.Y., USA). After 24 hours of transfections, the growth medium was replaced and CAP/Helium treatments were performed. TRIF imaging was carried out after 48 hrs of plasma treatments using Axiocam 506 mono camera (Carl Zeiss, Germany). Several fields (6-8) with numerous cells and about 300 (three separate experiments, n=3) particle vesicles containing TRAIL-R1 were analyzed at the cell surface. TIRF analysis was performed for only the particles that had movement, and these particles were chosen arbitrarily by the IMARIS software all along the cell borders. Images were recorded in the TIRF mode using the 488 nm laser scanner at 25 frames per second for a total of 15 minutes. Particle tracking was performed using the IMARIS software, and the distance, speed and tortuosity of the TRAIL-R1 particles were recorded.

Immunoblot

Cell lysates from CAP treated (0 and 48 hrs) ARPE-19 and Y-97 cells along with negative control and positive controls with $H_2O_2$ and TNF-α were isolated in RIPA buffer containing phosphatase and protease inhibitors (Thermo Fischer Scientific, Rockville, Md.). The V3 western workflow (Bio-Rad, Hercules, Calif.) consisted of stain free technology to calculate the total protein normalized to the immunodetected protein, namely NF-κB in the above samples using the ChemiDoc™MP Imager and Image Lab-™Software. The experiments were performed in triplicates and expressed as fold change further normalized to the untreated (naïve samples) cells (fold change of BCL-2/No treatment).

Q-PCR for BCL-2

Some of the above treated cells were used for detecting anti-apoptotic gene expression of BCL-2. RNA was isolated using Trireagent (Sigma Aldrich, St. Louis, MO, USA), first strand cDNA synthesis kit, superscript RT (Life Technologies, Long Island, NY, USA) and Green-2-Go qPCR mastermix (BioBasic, Ontario, Canada) was used to set up the experiment in the 96 well plate ((Bio-Rad, Hercules, Calif.). All experiments were performed in triplicates and from N=4samples. The following primers were used to amplify a 238bp product, namely forward primer GGATTGTGGCCT-TCTTTGAG (SEQ ID NO: 1) and reverse primer CCAAACTGAGCAGAGTCTTC (SEQ ID NO: 2) using CFX96 Touch System (Bio-Rad, Hercules, Calif.). The results were expressed as fold change of relative mRNA expression of BCL-2and further normalized to the untreated (naïve samples) cells using the Bio-Rad's automated CFX-Manager software.

Statistical Analysis

The following nonparametric tests for independent samples namely, NP tests/Independent Mann Whitney Wald Wolfowitz, pair wise Kruskal Wallis with median test value compared pair wise along with exclusion criteria of alpha=0.05 and CI level=95 were performed using SPSS software (Microsoft Corp, Seattle, Wash., USA).

Effect of CAP Treatments and Induction of Cell Death and Apoptosis

Two days after CAP treatments on Y-79 retinoblastoma cells and ARPE-19 normal cells, trypan blue dye exclusion test was carried out. The proportion of dead cells significantly increased at 1 and 2 minutes of CAP treatments in the tumor cells (87.6±16.38% and 90.74±16.04% respectively; FIG. 12). Although at 3 minute of CAP treatment there was 100% cell death, the respective control treatment with helium showed close to 50% cell death. Therefore 2 minutes of CAP was considered as threshold for inducing cell death in Y-79 cells. ARPE-19 normal cells were not affected by CAP or helium treatments. $H_2O_2$, a known mitochondrial oxidative cell stress inducer showed close to 100% cell death in both cell types (FIG. 12). To further determine the effect of CAP on Y-79 retinoblastoma and ARPE-19 normal cells, TUNEL DNA end labelling was carried out to quantify the apoptotic cells. Two minute CAP was sufficient to induce DNA nick and about 26% of Y-79 cells were apoptotic. Both the positive controls $H_2O_2$ and TNF-α showed 20-24% programmed cell death. However, ARPE cells remained unaffected and were negligible-to-negative for TUNEL labelling (FIG. 13).

Figure 14:
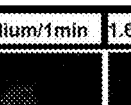
FIG. 14 is a table illustrating total surface expression of TRAIL-R1 at the cell Surface with CAP in ARPE-19 and Y79 cells. Confocal microscopic images were quantified for TRAIL-R1 using IMARIS software (A-F and M-R) (Green). In the presence of CAP, retinoblastoma cells showed significantly increased mean total fluorescence intensity (B and D; Arrow) than helium treated cells (A) and the ARPE-19 (M-R). Cells were counterstained for Mitosox (red) (G-L and S-X). Positive control $H_2O_2$ (E, Q) and CAP treatments showed mitochondrial cells stress (red positive cells; B-D and H-J, respectively). Note the absence of Mitosox positive cells and the double positive cells in ARPE-19 (S-X). DAPI counter stained nuclei (blue). Scale bar 10 μm.

Surface Expression of TRAIL-R1 in Response to CAP Treatment 3D reconstruction of z-stack images were quantified for total TRAIL-R1 protein expression at the cell surface. All the ARPE-19 normal epithelial cells had a base line expression of less than 4000 mean intensity (FIG. 14; M-R). However, Y79 cells expressed between 5000-6000 mean pixel intensity (FIG. 14, A, F), a characteristic of a tumor cell to express higher than normal amounts of TRAIL-R1 at the cell surface. In presence of CAP treatments for 1 minute, the expression of TRAIL-R1 was remarkably elevated to 8190.1±839.76 (FIG. 14, B), at two minutes 00000±00000 and three minutes the expression was reduced to 5454.73±1198.4. All the TRAIL-R1 positive cells in presence of CAP and $H_2O_2$ were positive for mitosox, a marker for ROS (FIG. 14).

TRAIL-R1 Vesicle Trafficking for Internalization

Figure 16:
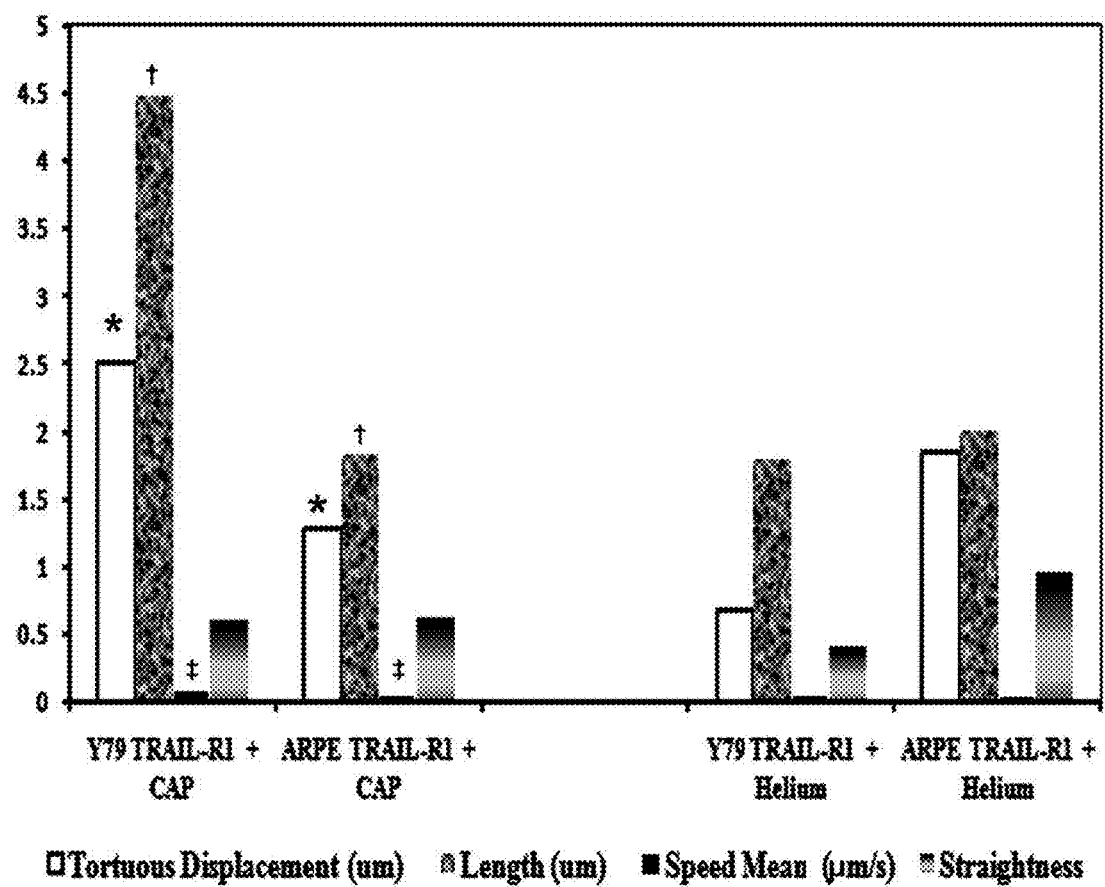
FIG. 16 is a graph showing the TIRF analysis of TRAIL-R1. A subset of TRAIL-R1 containing vesicles were long and the velocity and tortuous movement was significantly increased in this subset of retinoblastoma cells (*p≤0.05); Table 2). Note the absence of this subset in CAP treated ARPE-19 and Helium treated group.

Since total surface protein expression showed increased levels of TRAIL-R1, we carried out dynamic image analysis in live transfected cells. TRAIL-EGFP vector was transfected and then CAP treatments were performed followed by TIRF imaging. The Images were analyzed using IMARIS for vesicle internalization pattern of Y-79 and ARPE-19 cells. The table in FIG. 15 shows the particle length in Y-79 cells was significantly longer than the control cells or with helium treated cells, suggesting that the Y79 cells are trafficking and localizing at the cell surface. The tortuous movement of these particles and the speed or velocity of movement was significantly increased with CAP. These results suggest that there is a unique subset of vesicles (highly tortuous, lengthy with greater speed; FIG. 16) on the surface of the Y-79 cells allowing the trafficking machinery to recruit at the cell surface (FIGS. 14 and 16). The recruitment of all the particles at the cell surface may be indicative of a impedance in internalization or vesicular recycling of TRAIL-1 due to mitochondrial dysfunction and increased ROS (FIG. 14)

ROS/RNS Mediated Cell Stress in Presence of CAP 55-60% of cells treated with CAP were ROS positive in the Y-79 cells. In order to distinguish the species of cell stress inducer, intracellular RNS detection was carried out. In the tumor cells the RNS was detected between the ranges of 60-76% (FIG. 17), while normal cells showed negligible-to-negative expression of RNS. In general, both ROS and RNS were similarly expressed in response to CAP treatments.

Anti-Apoptotic Factors NF-κB and BCL-2 Expression in Presence of CAP

Figures 18A, 18B:
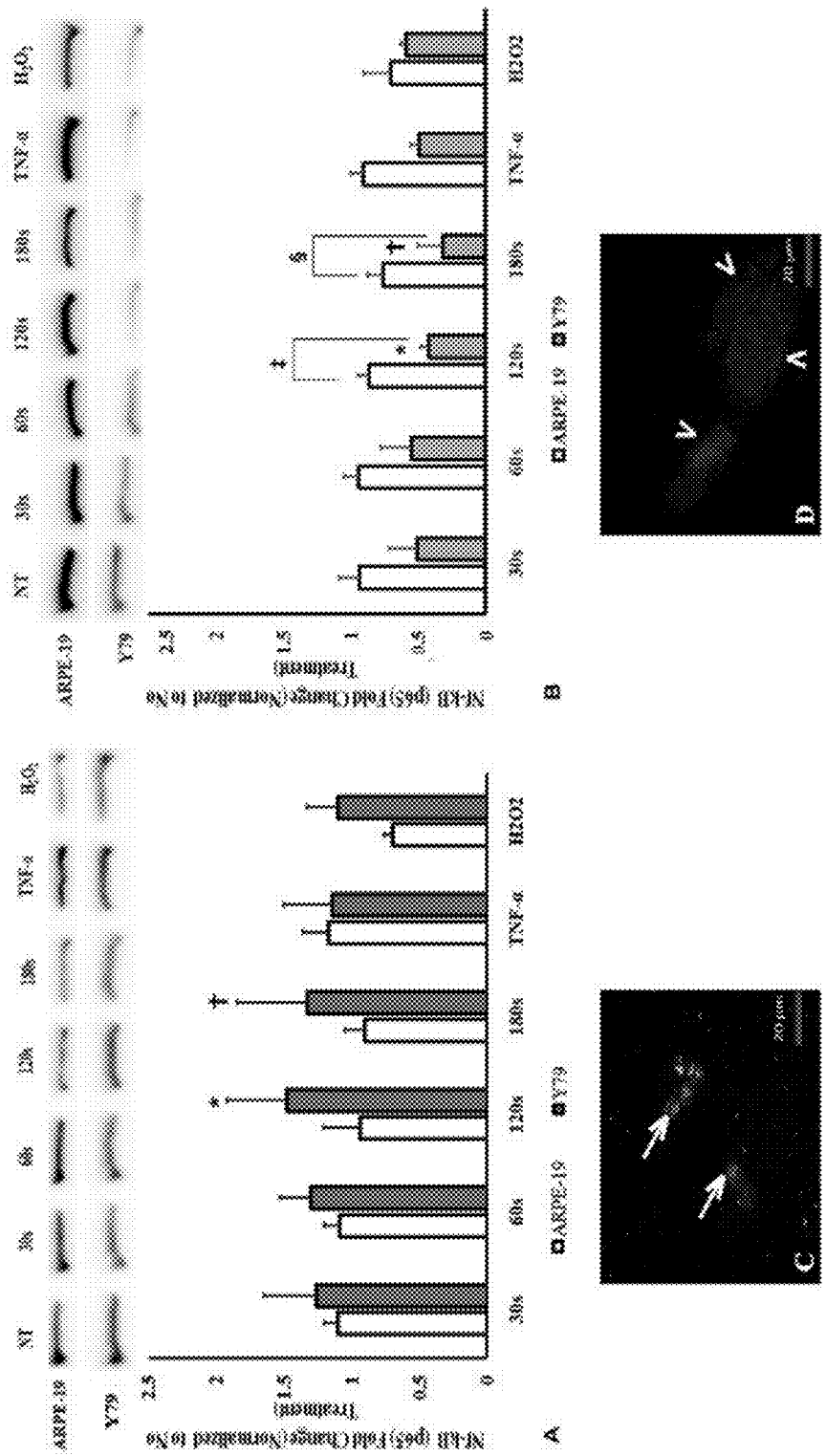
FIGS. 18A and 18B are tables showing total protein quantification for NF-κB p65 after CAP treatments in Y-79 and ARPE-19 cells. Cell lysates probed with anti-NF-κB p65 for samples immediately after CAP treatment show the cells are protected since both Y-79 and ARPE-19 cells expressed 1 to 1.5 folds of NF-κB p65 respectively (A). However 48 hours after CAP treatments these there was a significant decrease (*p≤0.05) in the expression of NF-κB p65 in Y-79 cells when compared to the ARPE-19 cells. The decrease was more profound in 2 and 3 minutes of CAP treatment in the Y-79 cells (B) suggesting that the cells are going through apoptosis.

NF-κB protein expression was 1 to 1.5 folds in the normal and tumor cells respectively immediately after treatments with CAP, suggesting that the cells were protected (FIG. 18A). After 48 hrs of treatment, the NF-κB expression was significantly reduced in the Y-79 when compared to the APRE-19 cells by more than 50% (FIG. 18B).

Moreover there was a two-fold decrease in the expression at 48 hrs when compared to 0 hr (FIGS. 18A and 18B), suggesting that the cells were subjected to apoptosis due to CAP treatments. Further, immunostaining for NF-κB showed a translocation from cytoplasm to the nucleus which was significantly higher in the Y79 cells after 2 minutes CAP treatments. Stimulation of Nf-κh and translocation towards the nucleus was significantly increased in the tumor cells and this pattern was absent in the normal retinal cells ($P \leq 0.05$; FIG. 19). The nuclear condensation in the apoptotic cells (Table 1) and significant increase ($P \leq 0.05$) in TUNEL positivity (FIGS. 18A and 18B) in corroboration with the activated NF-kb in the nucleus, suggests the hampered apoptotic machinery due to ROS mediated cell stress. 100±5.77% nuclear localization of Nf-κb was observed in the Y79 cells with 2 minute CAP treatment when compared to 19±0.63% in the ARPE-19 cells ($P \leq 0.05$). Moreover, increase in treatment time to 3 minutes showed a shift towards the nucleus even in the normal ARPE-19 cells (52±1.07%).

Figure 20A:
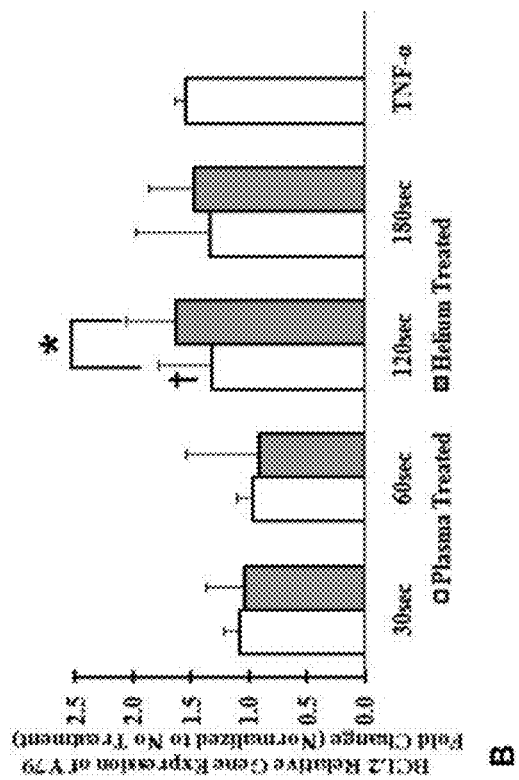
FIGS. 20A and 20B are bar graphs showing relative mRNA expression of Anti-apoptotic gene BCL-2 after 48 hrs of CAP treatment. The normal epithelial cells expressed 2 to 4 fold expression of BCL-2 after CAP treatments (A). Retinoblastoma cells not only show a 50% reduced expression when compared to the ARPE, but they were protected with significantly higher expression of BCL-2 mRNA in the helium treated Y-79 cells (B), suggesting that CAP induces apoptosis in the retinoblastoma cells at 2 minutes (*p≤0.05).
Figure 20B:
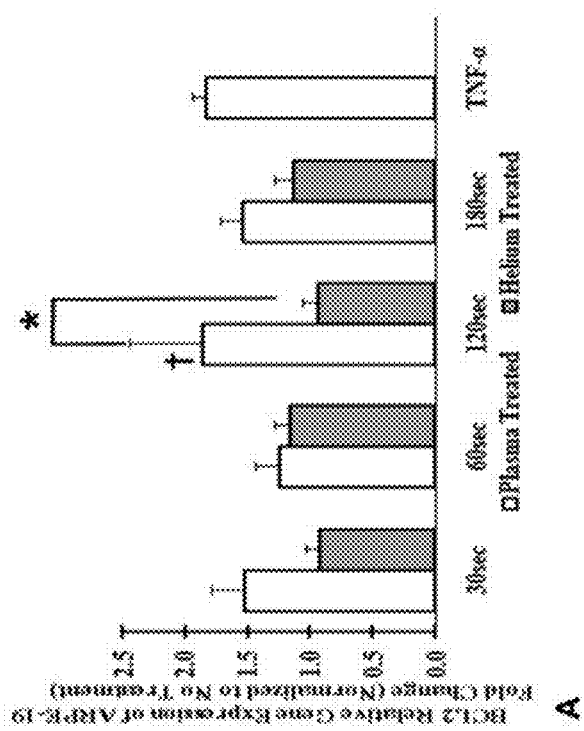

To study the upstream target of NF-κB, BCL-2 gene expression analysis was carried out. In ARPE-19 normal cells at 2 minutes of CAP there was a 4-fold expression BCL-2, whereas in Y-79 tumor cells in presence of CAP for 2 minutes, there was significantly reduced expression. It was interesting to note that helium treated controls were all protected with higher expression of the anti-apoptotic gene expression (FIGS. 20A and 20B).

Autophagy is a dynamic cellular protective process that occurs in response to stress and an abnormal microenvironment. Autophagy plays an important role during stress, starvation, degradation of damaged organelles etc. The influence of autophagy affects the mitochondrial recycle and modulates apoptosis via mitochondrial pathways. Autophagy contributes to bulk degradation of both cytoplasmic and mitochondrial damage. Recently, increasing evidence has indicated the importance of autophagy in human cancer, with autophagy exhibiting a dual function in cancer development. In healthy cells, autophagy acts as a tumor suppressor by clearing damaged proteins and organelle accumulation to prevent tumorigenesis. Example 3 shows that in the presence of CAP there is impaired recycling of TRAIL-R1 along with stimulation of mitochondrial superoxide (ROS and RNS) with concomitant accumulation of the receptor at the cell that triggers other downstream targets of NF-κB inducing apoptosis in retinoblastoma cells.

Figure 4:
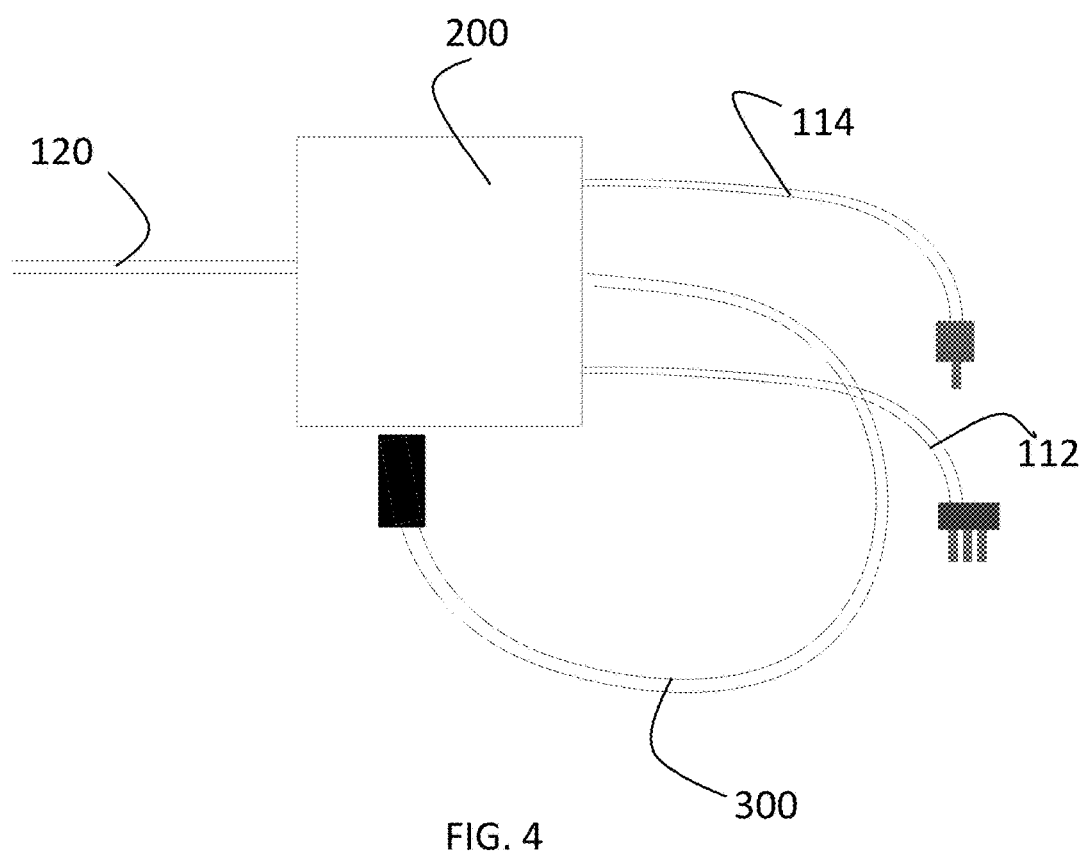
FIG. 4 is an illustrations of a CU with attached CPP in accordance with a preferred embodiment of the present invention.

It follows that CAP mediated cell death may occur through a mechanism of autophagy, wherein the normal cells are protected and the tumor cells displays impaired mictochondria or dysfunction due to cross-talk with the apoptotic machinery leading to cell death. TRAIL-R1 (DR4) trafficking at the cell membrane increases dynamically as detected by TIRF analysis we suggests that apoptosis is induced in a segregated pattern by membrane trafficking in presence of CAP in tumor cells (Table 2, FIGS. 2-4). The signaling molecules and the trafficking of proteins from interior to cell exterior, including mitochondrial transport machinery inducing autophagy malfunctioning that leads to various pathologies including retinoblastoma and other cancers. On the basis of the above literature and our current results, we suggest a mechanism by which CAP functions in retinoblastoma cells by triggering a cross talk between autophagy and apoptotic signals that collectively contributes to cell death. Consequently, CAP mediated apoptosis may be regulated by a mechanism of autophagy via the death receptor DR4 or TRAIL-R1 (FIGS. 1, 2).

Further, Example 3 demonstrates that TRAIL-R1 is responsible for initiating the cell death and apoptosis in the presence of CAP in tumor cells. There may be several mechanisms by which CAP affects TRAIL-R1 induced apoptosis. TNF-α mediated apoptosis has been reported to reduce BCL2 expression in retinoblastoma. CAP induced TRAIL-R1 induced apoptosis by reducing the protein and mRNA expression of Nf-kb and BCL2 respectively in an autocrine fashion. It is possible that p53 may be affected and there are paracrine signals that recruit TRAIL-R1 at the cell surface and would require further investigation.

TRAIL has been extensively used as a chemotherapeutic drug to treat breast and colon cancers. Our results demonstrate that CAP alone is sufficient to elevate TRAIL-R1 expression and thereby induce apoptosis. We demonstrate with quantitative confocal microscopy that total TRAIL-R1 protein expression in each cell upon CAP treatment in Y79 tumor cells was significantly higher when compared to the expression in ARPE-19 cells. It is interesting that CAP alone could selectively trigger death inducing signals in the retinoblastoma cells in vitro and not in the normal healthy cells by accelerating the TRAIL-R1 expression and inducing apoptosis. Selective increase in DR4 with CAP treatment suggests that CAP can potentially reduce the dose of the chemotherapeutic drug for cancer patients. This study therefore provides insights for application of CAP in cancer biology including retinoblastoma.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for elevating a TRAIL-R1 expression in cancer cells to induce apoptosis comprising the steps of:
receiving electrical energy having a first voltage, first frequency and first power from an electrosurgical generator;
up-converting the first voltage to a second voltage higher than said first voltage and down-converting the first frequency to a second frequency lower than said first frequency with a high voltage transformer having a ferrite core, a primary coil and a secondary coil, the primary coil being of a first gauge and having a first number of windings and the secondary coil having a second gauge and a second number of windings wherein the first gauge is larger than the second gauge and the second number of windings is greater than the first number of windings;
applying a converted electrical energy to an electrode in cold plasma probe;
flowing an inert gas through said cold plasma probe while said converted electrical energy is applied to said electrode to produce a cold plasma at a distal end of said cold plasma probe; and
applying said cold plasma to cancer cells for 1 to 3 minutes to elevate a TRAIL-R1 expression in said cancer cells to induce apoptosis of said cancer cells.

2. A method according to claim 1 wherein said inert gas comprises helium.

3. A method according to claim 1, wherein said cold plasma is applied to cancer cells for about 2 minutes.

4. A method for elevating a TRAIL-R1 expression in cancer cells to induce apoptosis comprising the steps of:
applying electrical energy having a voltage of 1.5-50 kV, a frequency less than 300 kHz and a power less than 2 W to an electrode of a cold plasma probe;
flowing an inert gas through said cold plasma probe while said electrical energy is applied to said electrode to produce a cold plasma jet at a distal end of said cold plasma probe; and
applying said cold plasma jet to cancer cells for 1 to 3 minutes to elevate a TRAIL-R1 expression in said cancer cells to induce apoptosis of said cancer cells.

5. A method according to claim 4 wherein said inert gas comprises helium.

6. A method according to claim 4, wherein said cold plasma is applied to cancer cells for about 2 minutes.

7. A method for treating cancer cells comprising the steps of:
receiving electrical energy having a first voltage and first frequency from an electrosurgical generator;
converting said received electrical energy to electrical energy having a second voltage and a second frequency with a high voltage transformer having a ferrite core, a primary coil and a secondary coil, the primary coil being of a first gauge and having a first number of windings and the secondary coil having a second gauge and a second number of windings wherein the first gauge is larger than the second gauge and the second number of windings is greater than the first number of windings;
applying said converted electrical energy to an electrode in cold plasma probe;
flowing an inert gas through said cold plasma probe while said converted electrical energy is applied to said electrode to produce a cold plasma jet at a distal end of said cold plasma probe; and
applying said cold plasma jet to cancer cells for 1 to 3 minutes.

8. A method according to claim 7 wherein said inert gas comprises helium.

9. A method according to claim 7 wherein said primary coil comprises 30AWG magnetic wire and said secondary coil comprises 36AWG magnetic wire.

* * * * *